United States Patent [19]

Koshiishi et al.

[11] 4,388,165
[45] Jun. 14, 1983

[54] SELECTIVE ION SENSITIVE ELECTRODE AND METHOD OF MAKING IT

[75] Inventors: Kiyozo Koshiishi, Sagamihara; Noriaki Ono, Hachiojo; Takashi Kamiyama, Tokyo; Yoshimi Kato, Hachiojo, all of Japan

[73] Assignee: Olympus Optical Company Ltd., Japan

[21] Appl. No.: 298,343

[22] Filed: Aug. 31, 1981

[30] Foreign Application Priority Data

Feb. 28, 1981 [JP] Japan .................. 56-26730[U]

[51] Int. Cl.³ ........................................... G01N 27/30
[52] U.S. Cl. .................................. 204/418; 427/125; 427/405; 427/409; 428/447
[58] Field of Search .................. 204/195 M; 427/409, 427/405, 125; 428/447

[56] References Cited

U.S. PATENT DOCUMENTS

| | | | |
|---|---|---|---|
| 3,957,613 | 5/1976 | Macur | 204/195 M |
| 4,052,285 | 10/1977 | Dobson | 204/195 G |
| 4,236,987 | 12/1980 | Schindler et al. | 204/195 M |
| 4,305,802 | 12/1981 | Koshiishi | 204/195 M |
| 4,315,970 | 2/1982 | McGee | 428/447 X |

FOREIGN PATENT DOCUMENTS

| | | | |
|---|---|---|---|
| 1558553 | 1/1980 | United Kingdom | 204/195 M |
| 544899 | 1/1977 | U.S.S.R. | 204/195 M |

*Primary Examiner*—G. L. Kaplan
*Attorney, Agent, or Firm*—Ostrolenk, Faber, Gerb & Soffen

[57] ABSTRACT

A selective ion sensitive electrode is so constructed that an ion exchanger sensitive to a specific ion is formed on a metal electrode, an electric conductive resin electrode or a chlorinated metal electrode to which a signal wire is connected so as to maintain a stable electric connection between the signal wire and the ion exchanger over a long period of time. A layer of a silane coupling agent is used between the electrode member and ion exchanger.

26 Claims, 8 Drawing Figures

SELECTIVE ION SENSITIVE ELECTRODE AND METHOD OF MAKING IT

BACKGROUND OF THE INVENTION

The invention relates to a selective ion sensitive electrode, and more particularly, to such electrode which may be used to determine the concentration of a specific ion contained in a solution to be examined.

There have been proposed various selective ion sensitive electrodes having an ion sensitive assembly which is selectively sensitive to a specific ion for determining the concentration of the specific ion by comparing a potential developed across an interface between a solution to be examined and the ion sensitive assembly when the latter is immersed into the former with a suitable reference potential. FIG. 1 illustrates an example of conventional selective ion sensitive electrodes. Such electrode is so constructed that a supporter 3 holding an ion exchanger 2 which is selectively sensitive to a specific ion is joined to one end of a stem 1 made from material such as glass, polyvinyl chloride or the like with adhesives 4 such as silicon RTV rubber manufactured by SHINETSU Chemical Co., Ltd. A signal wire 5 formed with coaxial cable has its one end connected to the supporter 3 by passing through the stem 1 and through the medium of an electric conductive resin 6. In the selective ion sensitive electrode thus formed, when the side of ion exchanger 2 which acts as an ion sensitive assembly is immersed into a solution to be examined an interface potential corresponding to the concentration of a specific ion may be developed across an interface between the ion exchanger 2 and the solution to be examined, thereby enabling a determination of the concentration of the specific ion to be made by detecting the interface potential.

However, because such a conventional selective ion sensitive electrode is formed so that the signal wire 5 is connected to supporter 3 or ion exchanger 2 through conductive resin 6, there are disadvantages in that its manufacturing is difficult, the joining strength between signal wire 5 and supporter 3 is small and a mechanical failure often occurs. Therefore an inconvenience is experienced in that stable use over a long term of time can not be expected.

SUMMARY OF THE INVENTION

It is an object of the invention to provide a selective ion sensitive electrode in which an ion exchanger selectively sensitive to a specific ion is formed on a metal electrode member, an electrically conductive resin electrode or a chlorinated metal electrode to which a signal wire is connected.

In accordance with the invention, an ion exchanger is formed on a metal electrode member or the like. Easy manufacturing of the selective ion sensitive electrode and stable performance of an electric connection between the signal wire and the ion exchanger over a long period of time are achievable.

DESCRIPTION OF THE PREFERRED EMBODIMENTS

Figure 2:
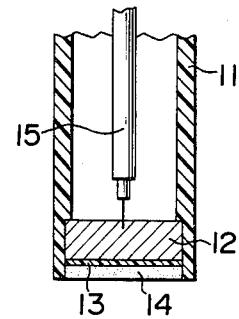
FIG. 2 is a cross section of a selective ion sensitive electrode according to an embodiment of the invention.

Referring now to FIG. 2, in which a selective ion sensitive electrode according to an embodiment of the invention is illustrated, the electrode has a disc-shaped metal electrode 12 fitted into one end of a stem 11 made from polyvinyl chloride. An ion exchanger 14 is formed so as to be substantially flush with the end plane of stem 11. This is achieved by applying or pouring a solution in which is dissolved an ion-exchange substance or the like which substance is selectively sensitive to a specific ion. This substance is dissolved in a volatile solvent which is applied to metal electrode member 12 over a layer of silane coupling agent 13. The solvent is then permitted to evaporate. Subsequently a signal wire 15 formed as part of a coaxial cable is directly connected to metal electrode member 12 (upper surface in the drawing) through stem 11.

The silane coupling agent 13, as is indicated by its molecular formula $R'Si(OR)_3$, includes more than one reaction radical (methoxy, silanol radical or the like) strongly joinable by chemically bonding an inorganic substance (glass, metal or the like) into a portion of its molecular formula and another reaction radical (vinyl, epoxy, methacryl, amino radical or the like) which chemically bonds with an organic substance (all kinds of synthetic resins). Consequently the silane coupling agent 13 acts as a mediator between inorganic and organic substances.

The effect of the silane coupling agent 13 differs depending upon a resin or an elastomer to be applied. By way of example, as to the silane coupling agent, NUC Silicones, manufactured by Japan Uniker Co., Ltd., A-186 [beta-(3,4 Epoxycyclohexyl)ethyltrimethoxysilane], A-187 (gamma-Glycidoxypropyltrimethoxysilane), and A-189 (gamma-Mercaptopropyltrimethoxysilane) are effective for polyvinyl chloride and in addition A-189, A-1100 (gamma-Aminopropyltrimethoxysilane) and A-1120 [N-beta-(aminoethyl) gamma-aminopropyl-trimethoxysilane] are suitable to nitrile.

On the other hand, in the selective ion sensitive electrode of the embodiment of the invention, the above-mentioned solution which forms ion exchanger 14, utilizes a blend of, for example tetrahydrofuran (THF), a supporting substance such as polyvinyl chloride (PVC) or dioctyl adipic acid (DOA) and an ion-exchange substance sensitive to a specific ion. When such solution is poured onto metal electrode member 12, THF, which is volatile, evaporates, whereby substances other than THF remain on the surface of metal electrode 12. Of the remaining substances, PVC may be chemically bonded with metal electrode member 12 by action of the silane coupling agent 13 as stated above. In addition, when a solution containing an ion-exchange substance is poured into polyvinyl chloride stem 11, a part of the inner wall thereof dissolves, thereby the stem 11 is bonded with the ion-exchanger 14 by merging of PVC supporting the ion-exchange substance after evaporation of the THF.

Figure 1:
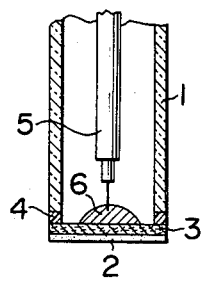
FIG. 1 is a cross section illustrating an example of conventional selective ion sensitive electrodes.

When the selective ion sensitive electrode of the embodiment thus formed is immersed in a solution to be examined, a potential corresponding to the concentration of a specific ion, as is the case with a conventional selective ion sensitive electrode illustrated in FIG. 1, may be developed across an interface between ion exchanger 14 and the solution to be examined, therefore permitting a determination of the specific ion concentration in the solution.

According to the electrode of the embodiment, the ion exchanger 14 is bonded with the PVC of stem 11 by action of THF in the solution and also is chemically bonded with the metal electrode member 12 by action of the silane coupling agent 13. Consequently a lowering of life of the electrode due to permeation of a solution to be examined between the stem 11 and the ion exchanger 14 can be avoided.

Furthermore, the signal wire 15 is directly connected to the metal electrode member 12, and not through a conductive resin, thus enabling the connection to be firm. As a result, it will be noted that with metal electrode member 12 and stem 11 firmly secured to ion exchanger 14, a selective ion sensitive electrode having a durable and compact construction and easy handling can be obtained.

In addition, compared with a conventional electrode, the one of the above embodiment has a smaller number of parts and therefore it is easier to manufacture. Thus these electrodes which are inexpensive and have uniform performance may be mass produced.

Still further, it should be understood that since ion exchanger 14 can be securely held on metal electrode member 12 its surface area can be increased. Thus a quick responding electrode is obtainable.

Figure 3:
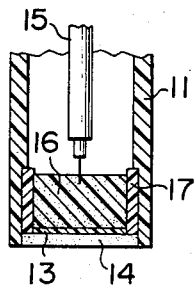
FIG. 3 is a cross section of a selective ion sensitive electrode according to another embodiment of the invention.

FIG. 3 illustrates a selective ion sensitive electrode of another embodiment according to the invention. The electrode has an electrode member 16 upon which is formed an ion exchanger 14. Member 16 is made from a thermoset conductive resin or a metal chloride. The electrode member 16 thus formed is fitted into one end of stem 11, electrode member 16 being held in an inner stem 17 made from glass or the same polyvinyl chloride as stem 11. This is a departure from the electrode shown in FIG. 2. Other members of the embodiment are constructed similarly to those of an electrode in FIG. 2. Accordingly, corresponding parts are designated by like reference numerals or characters without repeating their description. It is also to be noted that metal chlorides are generally easily obtainable by means of an electrochemical technique using a diluted hydrochloric acid solution.

It should be also understood that with the electrode of the embodiment thus formed the same function and effect as indicated in that shown in FIG. 2 can be obtained.

Figure 4:
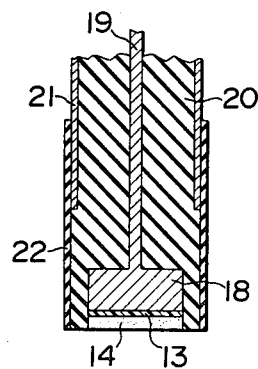
FIG. 4 is a cross section of a selective ion sensitive electrode according to a further embodiment of the invention.

FIG. 4 illustrates a selective ion sensitive electrode of a further embodiment of the invention. The electrode, in which a coaxial cable is not used as a signal wire, has a signal wire 19 integral with a metal electrode 18 by machining the metal electrode 18 associated with ion exchanger 14. The whole member thus formed except a portion of ion exchanger 14 in contact with a solution to be examined is covered with an insulating member 20. A metal stem 21 is disposed around the outer periphery of insulating member 20 so as to provide a shielding effect and another insulating member 22 is disposed around the outer periphery of metal stem 21 except a portion in engagement with an electrode holder (not shown in the drawing). In this case the ion exchanger 14, which is similar to the electrode shown in FIG. 2, is formed on a metal electrode 18 over the silane coupling agent 13.

The selective ion sensitive electrode of the embodiment has a function and an effect similar to that shown in FIG. 2. Since signal wire 19 and metal stem 21 of the electrode may also serve as a connector (compared to a conventional electrode which incorporates a BNC connector), its manufacturing cost can be advantageously decreased. Consequently, it is also noted that when the electrode has not carried out its function, it is interchangeable without changing a connector and also can be easily interchanged when the concentration of a different ion is to be determined.

Figure 5:
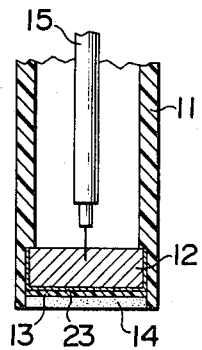
FIG. 5 is a cross section of a selective ion sensitive electrode according to a still further embodiment of the invention.

FIG. 5 illustrates a selective ion sensitive electrode of a still further embodiment of the invention. The electrode includes a conductive thin film 23 of 0.1 to 5$\mu$ thickness formed of corrosion resistant Au, Ag, Pt or an alloy thereof on the under and side surfaces (see FIG. 5) of metal electrode member 12 by an electrochemical technique, sputtering, CVD (Chemical Vapor Deposition) method, vacuum evaporation method or the like. An ion exchanger 14 is formed on the under surface of metal electrode member 12 which the conductive thin film 23 covers, over the layer of silane coupling agent 13. A signal wire 15 formed with a coaxial cable is directly connected to the upper surface of metal electrode member 12 within stem 11.

A corrosion resistant conductive thin film 23 is formed on metal electrode member 12 to solve the problem of limited life when a base metal such as Cu, Fe, Ni or the like or an alloy such as brass or the like is used to form metal electrode member 12. However, when a noble metal such as Au, Ag, Pt or the like having a good corrosion resistance is used for the entire electrode 12 cost is increased. Accordingly, in the electrode of the embodiment, a corrosion resistant conductive thin film 23 is formed on at least one surface of metal electrode member 12, in particular on at least the surface on which ion exchanger 14 is formed. An electrode member 12 can be formed with a high conductivity and low cost material such as Cu or the like and even when the thin film 23 is formed with a noble metal such as Au, Ag, Pt or the like the film thickness can be extremely small, therefore producing an inexpensive and durable electrode.

Figure 6A:
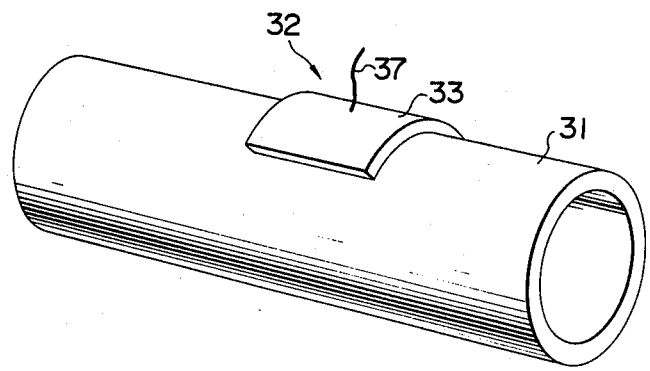
FIGS. 6(A) and (B) are an outside perspective view and a half cutaway perspective view of a selective ion sensitive electrode according to a still further embodiment of the invention.

FIGS. 6(A) and (B) illustrate a selective ion sensitive electrode of a still further embodiment of the invention. In this electrode, which is a through-flow type, a rectangular opening is formed on a part of a hollow insulating stem 31 through which a solution to be examined flows and an electrode assembly 32 is disposed over the opening so as to determine the concentration of a specific ion contained in the solution to be examined while the solution flows through the stem 31. The electrode assembly 32 is formed with a conductive thin film 34 of 0.1 to 5$\mu$ thickness made from a noble metal such as Au, Ag, Pt or the like on the inside of a saddle-shaped metal electrode 33 and an ion exchanger 36 is formed on the film 34 over a layer of silane coupling agent 35. The electrode assembly 32 is secured to the area of stem 31 around the opening with insulating adhesives such as epoxy resin or the like and a signal wire 37 is connected to the outer surface of metal electrode 33.

The electrode assembly 32, which is provided at a portion of hollow insulating stem 31, may be provided around the periphery thereof. Specifically a ring-shaped electrode is employed as metal electrode 33 and an ion exchanger 36 may be formed over a conductive thin film 34 and the layer of silane coupling agent 35 on the inner periphery of the electrode.

In the electrode of the above embodiment which is formed as a through-flow type, the same function and effect as indicated for the electrode shown in FIG. 5 are obtainable.

Figure 7:
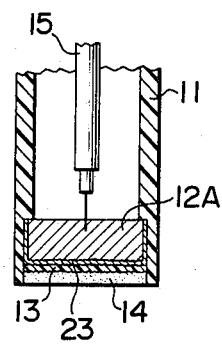
FIG. 7 is a cross section of a selective ion sensitive electrode according to a still further embodiment of the invention.

FIG. 7 illustrates a selective ion sensitive electrode of a still further embodiment of the invention. This electrode differs from the one shown in FIG. 5 only in that a surface of metal electrode member 12A on which an ion exchanger 14 is formed is made rough to the extent that the roughness is 1 to 100$\mu$ and a conductive thin film 23 is formed on the rough surface. It will be understood that when the surface of metal electrode members 12A on which thin film 23 is formed is made rough the adhesion between thin film 23 and ion exchanger 14 can be improved. It should be also understood that in the electrode of a through-flow type shown in FIGS. 6(A) and (B), if the inner surface of metal electrode 33 is made rough to the extent that the roughness is 1 to 100$\mu$ the adhesion between ion exchanger 36 and thin film 34 can be improved.

In each of the above-mentioned embodiments, while a metal electrode member includes an ion exchanger which is formed over a layer of silane coupling agent, if the adhesion between the metal electrode and the ion exchanger is strong the silane coupling agent may be dispensed with.

Figure 6B:
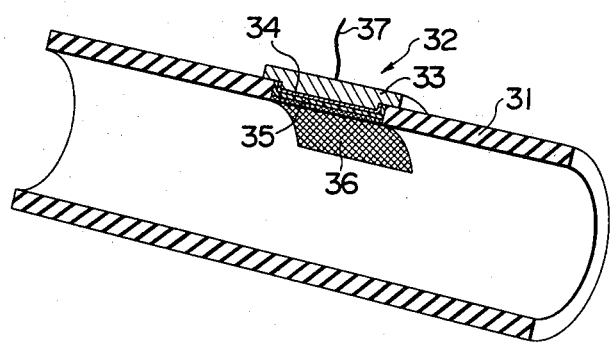

It is also to be noted that in the electrode of the embodiments of FIGS. 5 to 7, while a conductive thin film is formed on a surface of the metal electrode member on which an ion exchanger is formed, it may be formed so as to cover the whole surface of the metal electrode member.

What is claimed is:

1. A selective ion sensitive electrode including an ion exchanger selectively sensitive to a specific ion, comprising:
    an electrode member to which a signal wire is connected on one side thereof, said member comprised of one of a metal, an electrically conductive resin and a chlorinated metal;
    a corrosion resistant conductive thin film formed on the opposite side of said electrode member from said signal wire;
    a layer of a silane coupling agent on said corrosion resistant conductive thin film; and
    an ion exchanger formed on the surface of said layer of a silane coupling agent.

2. A selective ion sensitive electrode according to claim 1 in which the ion exchanger is formed by the process comprising the steps of applying a solution including at least an ion-exchanger substance, dissolved in a volatile solvent onto the layer of a silane coupling agent and allowing the solvent to evaporate.

3. A selective ion sensitive electrode according to claim 2 in which the solution further comprises a supporting substance selected from the group consisting of polyvinyl chloride and dioctyladipic acid.

4. A selective ion sensitive electrode according to claim 1 further comprising a stem in which the electrode member is held, the stem comprising a substance which is in part merged into the ion exchanger.

5. A selective ion sensitive electrode according to claim 1 in which the electrode member is comprised of a metal and the signal wire is integrally formed with the metal electrode member.

6. A selective ion sensitive electrode according to claim 5, further comprising an insulating member surrounding the signal wire and a metal stem surrounding the insulating member, the metal stem serving to shield the signal wire.

7. A selective ion sensitive electrode according to claim 1 in which the electrode member is a metal.

8. A selective ion sensitive electrode according to claim 7 in which the corrosion resistant conductive thin film is made from a noble metal.

9. A selective ion sensitive electrode according to claim 7 in which the ion exchanger is formed by the process comprising the steps of applying a solution including at least an ion exchange substance dissolved in a volatile solvent onto the conductive thin film and allowing the solvent to evaporate.

10. A selective ion sensitive electrode according to claim 7 in which the surface of the metal electrode member on which the ion exchanger is formed is made rough with a roughness of 1 to 100$\mu$.

11. A selective ion sensitive electrode according to claim 8 in which the noble metal is selected from the group consisting of gold, silver and platinum.

12. A selective ion sensitive electrode according to claim 10 further comprising a stem in which the electrode member is held, the stem comprising a substance which is in part merged into the ion exchanger.

13. A selective ion sensitive electrode according to claim 1 in which the signal wire is connected directly to the electrode member.

14. A sensitive ion selective electrode according to claim 13 in which the electrode member is comprised of a metal and the signal member is integrally formed with the metal electrode member.

15. A selective ion sensitive electrode according to claim 1, further comprising a housing for supporting said electrode member, said housing being formed from a nonconductive material, said electrode member being contained within an opening within said housing so that said ion exchanger is flush with a surface of said housing.

16. A selective ion sensitive electrode according to claim 15, further comprising an inner housing member for holding said electrode member, said inner housing member being received within said opening.

17. A selective ion sensitive electrode according to claim 16 in which the corrosion resistant conductive thin film is made from a noble metal.

18. A selective ion sensitive electrode according to claim 15 in which said housing is formed as a cylindrical tube adapted to receive a liquid therein, said tube having an inner cylindrical surface, an outer cylindrical surface and an opening in said tube between said inner and outer surfaces, said electrode member being formed to conform to said outer surface adjacent said opening and to cover said opening, said ion exchanger being flush with said inner surface.

19. A selective ion sensitive electrode according to claim 18 in which the electrode member is ring-shaped and extends around the periphery of the cylindrical tube.

20. A selective ion sensitive electrode according to claim 19 in which the corrosion resistant conductive thin film is made of a noble metal selected from the group consisting of gold, silver and platinum.

21. A selective ion sensitive electrode according to claim 18 in which the surface of the electrode member on which the ion exchanger is formed is made rough with a roughness of 1 to 100μ.

22. A selective ion sensitive electrode according to claim 15 in which the electrode member is a metal.

23. A process of forming a selective ion sensitive electrode comprising the steps of providing an electrode member to which a single wire is connected on one side thereof, said member comprised of one of a metal, an electrically conductive resin and a chlorinated metal, a corrosion resistant conductive thin film formed on the opposite side of said member from said signal wire and a layer of a silane coupling agent on the surface of said corrosion resistant conductive thin film; applying a solution having an ion exchange substance dissolved in a volatile solvent to the surface of said layer of silane coupling agent; and allowing the solvent to evaporate to form an ion exchanger on said layer of silane coupling agent.

24. The process of claim 23, further comprising the step of inserting the electrode member into an opening in a stem in which the electrode member is held before applying the solution.

25. The process of claim 24 in which the electrode member is inserted to a depth in the opening so that the ion exchanger formed is flush with a surface of the stem.

26. The process of either of claims 24 or 25 in which the portion of the stem is partly merged into the ion exchanger due to the action of the solvent upon the stem.

* * * * *